US00PP08631P

United States Patent [19]

Tulp

[11] Patent Number: Plant 8,631

[45] Date of Patent: Mar. 8, 1994

[54] HYBRID TEA ROSE PLANT NAMED RUITULVI

[75] Inventor: P. C. Tulp, Kudelstaart, Netherlands

[73] Assignee: de Ruiter's Nieuwe Rozen B.V., Hazerswoude, Netherlands

[21] Appl. No.: 999,224

[22] Filed: Dec. 31, 1992

[51] Int. Cl.[5] ..... A01H 5/00

[52] U.S. Cl. ..... Plt./18

[58] Field of Search ..... Plt. 18, 19

*Primary Examiner*—Howard J. Locker

*Attorney, Agent, or Firm*—Christie, Parker & Hale

[57] ABSTRACT

A new variety of hybrid rose plant having medium pink flowers.

2 Drawing Sheets

SUMMARY OF THE INVENTION

The present invention relates to a new and distinct variety of rose plant of the hybrid tea rose class, which was discovered by me as a natural whole plant mutation of the variety known as 'Ruidriko' (U.S. Plant Pat. No. 7,362) in a controlled, cultivated planting of the parent variety in Kudelstaart, The Netherlands. The varietal denomination of the new variety is 'Ruitulvi'.

Among the novel characteristics possessed by this new variety which distinguish it from its parent and all other varieties of which I am aware are its attractive medium pink flowers borne on a plant having the same advantageous qualities of its parent, 'Ruidriko', for production of cut flowers under glass. In contrast to the medium pink flowers of the new variety, the parent produces flowers of light peach/apricot to light pink coloration. The new variety can be reproduced through propagation by cuttings, grafting, budding and micropropagation. Flowers of the new variety are produced on long strong stems. Asexual reproduction by budding, grafting, propagation of cuttings, and micropropagation of the new variety as performed in Hazerswoude, Holland, shows that the foregoing and other distinguishing characteristics come true to form and are established and transmitted through succeeding propagations.

BRIEF DESCRIPTION OF ILLUSTRATIONS

The accompanying illustrations show typical specimens of the vegetative growth and flowers of the new variety in different stages of development depicted in color as nearly true as it is reasonably possible to make the same in a color illustration of this character. Colors may vary depending upon growing conditions under different climate, soil, and cultivation conditions.

One illustration shows cut flower form of the new variety and the other illustration shows details of the new rose variety.

DETAILED DESCRIPTION OF THE NEW VARIETY

The following is a detailed description of my new variety, with color terminology in accordance with the Royal Horticultural Society Colour Chart (RHSCC) and horticultural terminology in accordance with standard terminology used in UPOV-approved horticultural guidelines. The terminology used in color descriptions herein refers to plate numbers in the aforementioned color chart.

Parentage: Mutation of variety 'Ruidriko'.
Class: Hybrid tea.

As can be seen in the accompanying detailed illustration there is shown the top of a young shoot, 1; compound three, five and seven leaflet leaves, 2, 3, and 4 respectively; a stem, 5; buds, 6 and 7; a flower, 8, about one-third open; and a flower 9, more fully open. Also shown are flower stems 10, 11 and 12, with reproductive organs displayed.

The following further horticultural observations were made of specimens grown under glass in Holland.

Flower

Blooming Habit: Nearly continuous.

A. Bud:

(1) *Size.*—Medium.

(2) *Form.*—Ovate (before separation of sepals); urn-shaped after sepals part and petals begin to unfurl.

(3) *Color.*—As sepals divide, bud color is near 62A to 62B washing into very pale pink; deeper coloration at petal edge of bud.

(4) *Sepals.*—About same length as bud, generally simple, a few extensions.

(5) *Peduncle.*—Length — about medium to long. Aspect — straight. Strength — erect, very strong. Color — medium green.

B. Bloom:

*Flower.*—Large size; viewed from above — irregularly rounded; viewed from side — (a) side view of upper part of fully opened flower, flattened convex; (b) lower part of fully opened flower, flattened convex; large petals.

(1) *Size.*—Average size when fully expanded — about 15 cm.

(2) *Borne.*—Singly, one to a stem.

(3) *Form.*—Ovoid, spiral imbricated, high center, exhibition type, becoming flat; recessed center; outer petals reflex and quill to points; mid petals reflex and roll under slightly.

(4) *Petalage.*—Many petaled under normal conditions — fully double, about 25 petals.

(5) *Color.*—When sepals separate and petals begin to unfurl, near 62A to 62B with near 55C to 55D washing; color of undersurface is somewhat lighter. Deeper tonality appears where petals bunch. Coloring at point of petal attachment is near 56D. Overall tonality from a distance is very attractive pink. Substantially nonfading upon aging.

(6) *Pedicel.*—Very few to no hairs or prickles.

(7) *Fragrance.*—Slight to none.

C. Petals:

(1) *Texture.*—Medium.

(2) *Appearance.*—Inside and outside velvety.

(3) *Form and size.*—Large, transverse elliptic.

(4) *Arrangement.*—Regularly arranged, imbricated.

(5) *Petaloids in center.*—Few to none.

(6) *Lasting quality.*—Long-lasting quality on plant and after cutting.

Reproductive Organs

A. Stamens, filaments and anthers:

*Arrangement and color.*—Regularly arranged around styles; color of filaments is very pale yellow.

B. Pollen:

*Color.*—Deep yellow.

C. Styles: Long, stigma above mouth of receptacle, red.

D. Stigmas: Positioned below anthers.

E. Hips: Funnel-shaped.

Plant

A. Form: Narrow bushy.

B. Growth: Vigorous, to medium height, about 1.8 meters.

C. Foliage: Compound 3, 5 and 7 leaflets.

(1) *Size.*—Medium.

(2) *Quantity.*—Abundant.

(3) *Color.*—Foliage at time of first flowering — medium green.

(4) *Shape.*—Oval, pointed.

(5) *Texture.*—Upper side is medium to weakly glossy; underside is matte.

(6) *Edge.*—Serrate.

(7) *Serration.*—Ordinary, acuminate apices.

(8) *Leaf stem.*—Color — medium green.

(9) *Stipules.*—Short, simple, medium to dark green, distinct auricle.

(10) *Leaflets.*—Cross section — slight convex; little (weak) undulation at margin; terminal leaflet — medium length and width (of blade), wedge-shaped base; petiole — long.

(11) *Stem.*—Length: About 80 cm.

D. Wood:

(1) *New wood.*—Color — young shoots have weak anthocyanin coloration — bronze to reddish brown.

(2) *Old wood.*—Color — medium green.

E. Prickles (thorns):

(1) *Prickles.*—Present; quantity (main stalk) — ordinary; On laterals from stalk — ordinary; Shape of lower side — highly concave; Length — very few $\leqq 5$ mm; long $> 5$ mm — few to medium; Color — tan; Position — irregular.

I claim:

1. A new and distinct variety of rose plant of the hybrid tea rose class, substantially as shown and described.

* * * * *

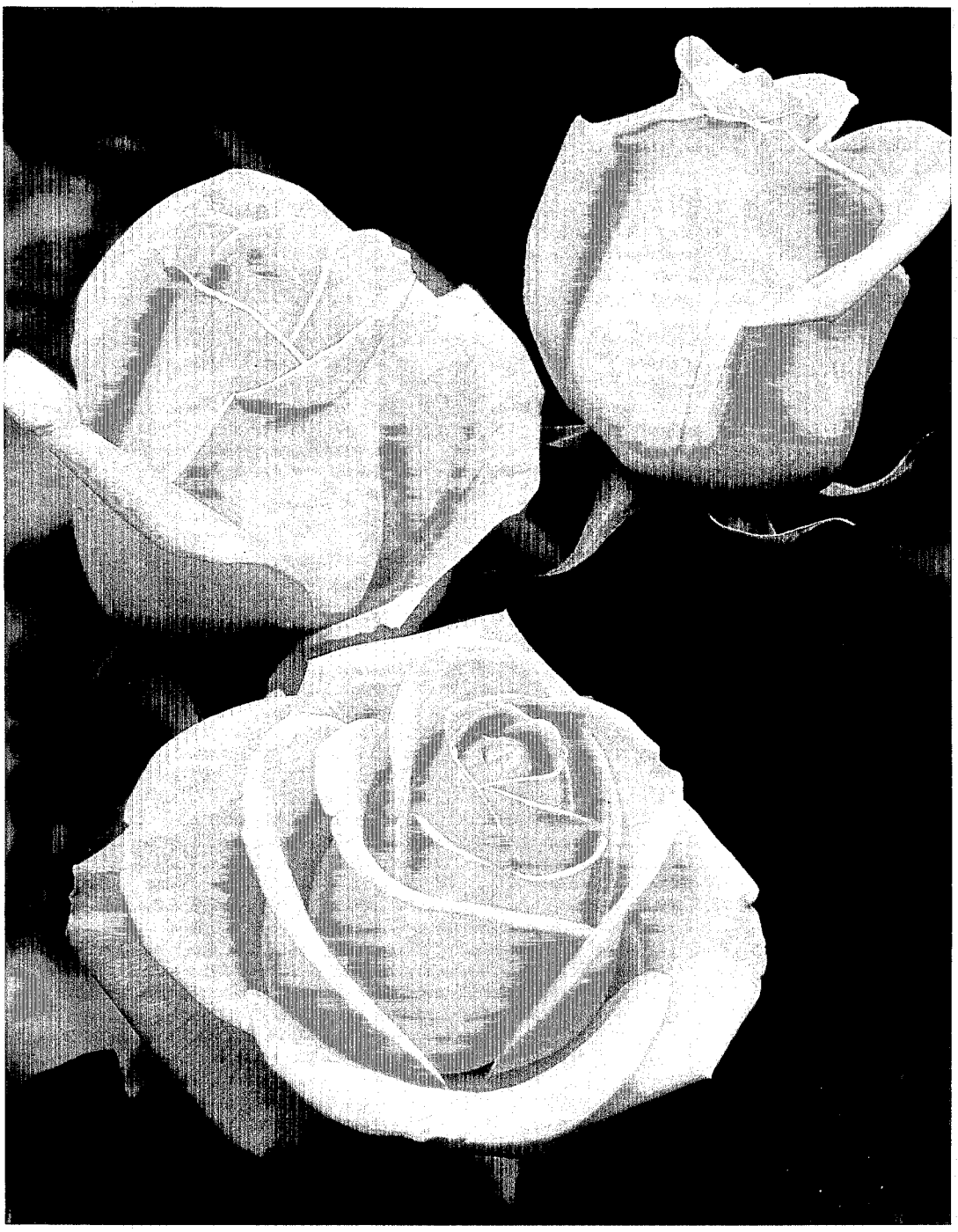

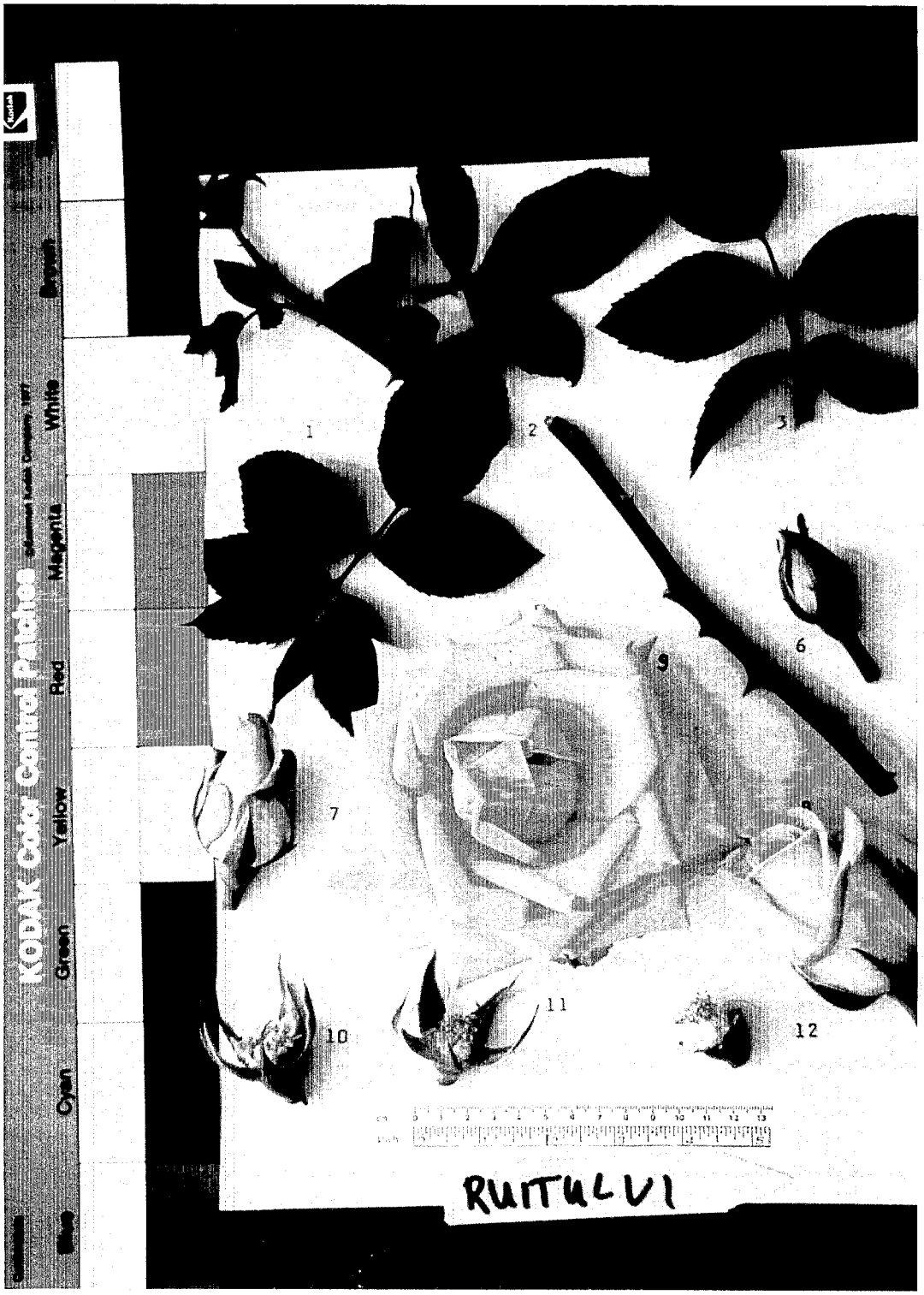
KODAK Color Control Patches
Blue
Cyan
Green
Yellow
Red
Magenta
White
Brown
1
2
3
4
5
6
7
8
9
10
11
12
RUITULVI

UNITED STATES PATENT AND TRADEMARK OFFICE

CERTIFICATE OF CORRECTION

PATENT NO. : Plant 8,631

DATED : March 8, 1994

INVENTOR(S) : P.C. Tulp

It is certified that error appears in the above-indentified patent and that said Letters Patent is hereby corrected as shown below:

On title page, item

[56] References Cited, U.S. PATENT DOCUMENTS, after "[58]" insert the following reference:
-- [56] Reference Cited
U.S. PATENT DOCUMENT
P.P. 7,362 10/1990 De Ruiter...Plt. 18 --.

Signed and Sealed this

Twenty-ninth Day of November, 1994

*Attest:*

Bruce Lehman

BRUCE LEHMAN

*Attesting Officer*

*Commissioner of Patents and Trademarks*